United States Patent [19]
Vlaminck et al.

[11] Patent Number: 6,113,937
[45] Date of Patent: *Sep. 5, 2000

[54] SUSTAINED RELEASE SUFENTANIL COMPOSITIONS

[75] Inventors: Kathleen Marie Jeanne Alice Vlaminck, Vosselaar; Marc Karel Jozef François, Kalmthout; Christiane Gabriella Gerarda Maria Heyns, Vosselaar, all of Belgium

[73] Assignee: Janssen Pharmaceutica, N.V., Beerse, Belgium

[ * ] Notice: This patent issued on a continued prosecution application filed under 37 CFR 1.53(d), and is subject to the twenty year patent term provisions of 35 U.S.C. 154(a)(2).

[21] Appl. No.: 09/087,668

[22] Filed: May 15, 1998

[51] Int. Cl.⁷ .......................... A61K 9/08; A61K 31/445
[52] U.S. Cl. ............................................ 424/422; 514/327
[58] Field of Search .............................. 424/422; 514/336, 514/327

[56] References Cited

U.S. PATENT DOCUMENTS 5,446,070  8/1995  Mantelle ............................... 514/772.6

FOREIGN PATENT DOCUMENTS 2 287 404    9/1995   United Kingdom .
92/02256     2/1992   WIPO .
WO 95/31182 11/1995   WIPO .

*Primary Examiner*—Thurman K. Page
*Assistant Examiner*—Alysia Berman
*Attorney, Agent, or Firm*—Ellen Ciambrone Coletti

[57] ABSTRACT

The present invention concerns sustained release sufentanil compositions for intramuscular administration, the preparation of said compositions and the use of said compositions for inhibiting pain, in particular post-operative pain, in animals, particularly in companion animals.

14 Claims, No Drawings

SUSTAINED RELEASE SUFENTANIL COMPOSITIONS

The present invention concerns sustained release sufentanil compositions for intramuscular administration, the preparation of said compositions and the use of said compositions for inhibiting pain, in particular post-operative pain, in animals, particularly in companion animals.

Sufentanil is the generic name of N-[4-(methoxymethyl)-1-[2-(2-thienyl)ethyl]-4-piperidinyl]-N-phenylpropanamide and can be represented by the formula

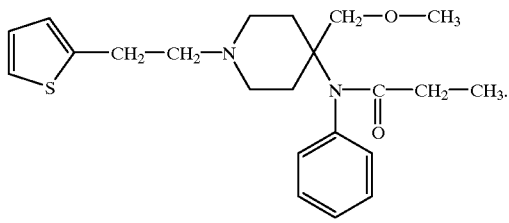

This compound, its acid addition salt forms, preparation and pharmacological properties are known from U.S. Pat. No. 3,998,834. Sufentanil is a potent, short-acting opioid analgesic; 7 to 10 times as potent as fentanyl and 500 to 700 times as potent as morphine. Sufentanil is known to provide cardiovascular stability and attenuation of stress reactions with minimal side-effects and without compromising recovery. In humans, it has been used, intravenously, as an adjunct to nitrous oxide/oxygen in general surgery and at higher doses ($\geq 8$ μg/kg) as a sole anaesthetic in cardiac and neurosurgery.

It is not uncommon that human patients and also animals suffer pain following a surgical procedure. Sufentanil's use for the control of such acute pain in human patients and in animals by conventional or intramuscular or intravenous administration has been limited because of its short duration of action. In human patients, this problem can be overcome by a continuous infusion or by regular injections at fixed intervals of about 2 to 4 hours. However, drawbacks of continuous infusion are for example the need of an infusion device, the need for continuous supervision and the high cost. Most certainly, continuous infusion is impractical, and in many instances not fit, for use in veterinary medicine. Also, the use of intramuscular injections of shortacting opioids at fixed intervals has it handicaps. A common failure of pain relief therapy occurs through the persistent use of shortacting medications on an "as needed" basis. A major disadvantage of this patient-controlled analgesia is that the indication for analgesic therapy (pain) occurs before the drug can be administered. It may then take time and higher doses of opioids to relieve the pain and usually leads to a cycle of undermedication and pain, alternating with periods of overmedication and drug toxicity. Thus, while intramuscular injection of shortacting opioids is a simple and inexpensive technique, it falls short in achieving an efficacious control of acute pain. Moreover, patient-controlled analgesia is impossible in veterinary medicine. Administration of analgesics by the owner or by a veterinarian will seldom be programmed "just-in-time". Other drawbacks of current pain relief therapies include concerns about respiratory depression and drug dependency associated with opioid analgesics.

The ideal therapeutic regimen for acute pain relief would be to achieve rapidly therapeutic plasma levels and to maintain these for extended periods (if required) without undue side-effects such as respiratory depression.

WO-92/02256, published on Feb. 20, 1992, discloses a pharmaceutical composition comprising sufentanil citrate and 2-hydroxypropyl-β-cyclodextrin useful for neuraxial administration. UK patent application GB-2,287,404, published on Sep. 20, 1995, encompasses compositions for the prevention or treatment of pain or inflammatory diseases which comprise a substance P receptor antagonist and an antiinflammatory or analgesic agent, such as, e.g. sufentanil. WO-95/31182, published on Nov. 23, 1995, discloses formulations, useful for aerosol delivery with a metered dose inhaler, comprising a base form of a narcotic drug such as, e.g. sufentanil, and a propellant. Optionally lubricants such as saturated vegetable oils, e.g. fractionated coconut oils, may be present to lubricate valves in said metered dose inhaler.

The present invention now provides specific pharmaceutical compositions suitable for intramuscular administration, comprising a medium-chain triglyceride as a carrier and as an active ingredient an effective analgesic amount of sufentanil. Said compositions are particularly useful in veterinary medicine and give a constant sustained release of sufentanil over a period ranging from 12 to 48 hours, in particular 24 hours, and retain all advantageous properties of the known short-acting sufentanil compositions. Therapeutic plasma levels can be achieved rapidly and maintained for the above periods.

The term "medium-chain triglyceride" as used hereinabove defines triglycerides of saturated fatty acids, in particular of octanoic (caprylic) and decanoic (capric) acid. Said triglycerides correspond to the requirements laid down in the European Pharmacopoeia EP93 (Triglycerida saturata media), the British Pharmacopoeia BP88 (Fractionated coconut oil) and the DAB 9 (Mittelkettige Triglyceride). Synonyms for medium-chain triglyceride are, for example, fractionated coconut oil, thin vegetable oil, mittelkettige Triglyceride, triglycerida mediocatenalia and are meant to be comprised under the term "medium-chain triglyceride" as used herein. A particular example of said triglycerides is Miglyol 812®, a substantially colourless, odourless, tasteless, neutral and stable, oil-like liquid with low viscosity. Comparable medium-chain triglycerides are Estasan GT8-40 35/78®, Myritol 318® and the like.

The term "sufentanil" as used in the specification and the claims herein comprises sufentanil in the free base form and in particular the salts thereof which are soluble in medium-chain triglycerides, especially salts of sufentanil with $C_{8-22}$carboxylic acids, including saturated and unsaturated $C_{8-22}$carboxylic acids.

Said $C_{8-22}$carboxylic acids are meant to comprise those carboxylic acids having from 8 to 22 carbon atoms such as, for example octanoic (caprylic), nonanoic (pelargonic), decanoic (capric), undecanoic, lauric, tridecanoic, tetradecanoic (myristic), pentadecanoic, hexadecanoic (palmitic), heptadecanoic, octadecanoic (stearic), nonadecanoic, eicosanoic, heneicosanoic and docosanoic acid. Examples of unsaturated $C_{8-22}$carboxylic acids include oleic, linoleic, linolenic acid and the like.

Particular salt forming carboxylic acids are $C_{8-22}$carboxylic acids, preferably myristic, palmitic, stearic and eicosanoic acid, more preferably stearic acid.

Most preferred are compositions wherein sufentanil and stearic acid are formulated in stoechiometric amounts, i.e. sufentanil in its (1:1) stearic acid salt form.

In the compositions according to the present invention the concentration of sufentanil in free base form ranges from 0.1 mg/ml to 1 mg/ml, in particular from 0.3 mg/ml to 0.8 mg/ml. Preferably, the concentration of sufentanil in free base form is 0.5 mg/ml.

If desired, other active ingredients may be incorporated in the present compositions, such as, for example, antimicrobials, antioxidizing agents or a combination thereof, e.g. methyl parahydroxy benzoate, ethyl parahydroxybenzoate, salicylic acid, benzoic acid, benzyl alcohol, butylhydroxytoluol, butylhydroxyanisole, propylgallate, ascorbylpalmitate, α-tocopherol and the like. The individual concentration of said other active ingredients in the present compositions is small, in general less than 2% (w/w).

Preferred compositions contain an appropriate amount of an antimicrobial, more in particular, benzyl alcohol, and/or an appropriate amount of an antioxidizing agent such as, for example, butylhydroxytoluol, butylhydroxyanisole, propylgallate, ascorbylpalmitate, α-tocopherol or a combination thereof.

Preferably, BHT (also known as butylated hydroxytoluene, butylhydroxytoluol or 2,6-di-tert-butyl-4-methylphenol) is used as an antioxidizing agent in an amount between 0.1 and 1 mg/ml, in particular 0.25 mg/ml.

For preparing the compositions of the present invention, the active ingredient sufentanil in its free base form or in its salt form as defined hereinabove, is intimately mixed with a medium-chain triglyceride. Compositions comprising a salt of sufentanil with a carboxylic acid as defined hereinabove may also be prepared by intimately mixing said carboxylic acid in the medium-chain triglyceride at a temperature ranging between room temperature and 60° C., preferably between 40° C. and 50° C., prior to intimately mixing the active ingredient sufentanil in its free base form. Where appropriate, one or more other active ingredients as defined hereinabove may be added to the admixture. The thus obtained solutions are then brought to the final volume by the addition of medium-chain triglyceride as required. The addition of the required amount of the medium-chain triglyceride may also be performed at an earlier time during the preparation procedure. The resulting oil solution of sufentanil may be sterilized by filtration and filled in sterile ampoules. If desired, the resulting oil solution may be filled in said sterile ampoules under an inert atmosphere such as, for example, oxygen-free nitrogen. Optionally, said ampoules may be made of amber colored glass.

An interesting preparation procedure comprises the following steps (a) intimately mixing a carboxylic acid with a medium-chain triglyceride;

(b) intimately mixing sufentanil in free base form with a solution of a carboxylic acid in a medium-chain triglyceride;

(c) intimately mixing one or more active ingredients with a solution of a carboxylic acid and sufentanil in free base form in a medium-chain triglyceride;

(d) filtering a solution of a carboxylic acid and sufentanil in free base form and one or more other active ingredients in a medium-chain triglyceride under sterile conditions;

(e) filling a filtered solution of a carboxylic acid and sufentanil in free base form and one or more other active ingredients in a medium-chain triglyceride in sterile ampoules.

The present compositions may be formulated in dosage unit forms or in multi-dose containers. It is especially advantageous to formulate the present compositions in multi-dose containers. A multi-dose container as used herein refers to a physically discrete container containing between 1 and 10 ml, more preferably between 2 ml and 5 ml, of one of the present compositions, and from which multiple unitary dosages may be taken. A multi-dose container may have the advantage that a physician or a veterinarian can select on the basis of the diagnosis of the subject to be treated the appropriate amount, and if desired, that the multi-dose container may be stored and used afterwards to treat the same or a different subject.

The present invention further relates to the pharmaceutical compositions as defined hereinabove for use as an analgesic. In particular, the present invention relates to the use of the present pharmaceutical compositions for preparing a medicament to treat animals suffering from acute pain, more in particular post-operative pain.

Pain as used herein relates to post-operative pain following surgery, including dental surgery; cancer pain; pain occurring while a veterinary surgeon performs an intervention which does not require general anesthesia such as, for example, in case a veterinary surgeon treats an ear infection; post-traumatic pain and the like instances of acute pain.

Thus, the present invention provides a method of inhibiting pain, particularly acute pain, more in particular post-operative pain, in an animal, in particular companion animals, comprising administering intramuscularly to said animal a therapeutically effective amount of a composition as defined hereinabove.

The intramuscular injection of the present compositions may be administered just prior to surgery or at the end of surgery, preferably during the early postoperative period. Said injection can conveniently be given in, for example, the musculus gluteus with, for example, the use of an appropriate intramuscular needle with long bevel.

Companion animals as used herein are meant to include all animals that are not used for the production of food. Examples of companion animals are dogs, cats and the like.

In order to achieve rapidly therapeutic plasma levels and to maintain these for extended periods (if required) without undue side-effects such as respiratory depression, and, depending on the species, it is contemplated that an effective amount of sufentanil would range from 25 µg/24 h to 25 mg/24 h, preferably from 100 µg/24 h to 10 mg/24 h of the active ingredient sufentanil in free base form, in order to obtain effective analgesia with therapeutic plasma levels in the range of from 0.3 ng/ml to 3 ng/ml, in particular from 0.85 ng/ml to 1.5 ng/ml. Taking into account the body weight of the subject to be treated, said required therapeutic plasma levels, and hence, the desired clinical effects can be obtained by administering intramuscularly a dose ranging between 25 µg/kg body weight to 75 µg/kg body weight, preferably a dose ranging between 35 µg/kg body weight to 70 µg/kg body weight, more preferably a dose of 50 µg/kg body weight of the active ingredient sufentanil in base form. Using a composition comprising 0.5 mg/ml of sufentanil in free base form, e.g., an animal weighing about 50 kg should receive about 5 ml of the composition, animals weighing about 5 kg should receive 0.5 ml of the composition. Obviously these doses may be lowered or increased, depending on the severity of the pain, the individual response of the animal and the required duration of effective analgesia. Further, if deemed necessary, the present composition may be administered repeatedly at appropriate intervals, e.g. at 12 hour or longer intervals, preferably at 24 hours intervals.

Pharmacokinetic studies as presented in the experimental part B hereinafter show that therapeutic plasma concentrations may be obtained soon after injection of a 0.5 mg/ml solution at a dose ranging between 35 μg/kg body weight and 70 μg/kg body weight, and are maintained for up to 48 hours after injection.

The following examples are intended to illustrate the present invention and not to limit the scope thereof.

Experimental Part

A. Preparation of the Compositions

Formula F.1: Injectable Solution—0.5 m/ml

Miglyol 812® (500 grams) was stirred at 46° C. and stearic acid (1.85 grams) was added. Stirring was continued for 30 minutes. While stirring, the solution was diluted with Miglyol 812® (4140 grams). The resulting solution was allowed to cool to room temperature, and sufentanil in its free base form (2.5 grams) was added. Stirring was continued for 16 minutes. Benzyl alcohol (75 grams) was added while stirring at room temperature. The resulting solution containing 0.5 mg/ml of the active ingredient sufentanil was filtered under sterile conditions and filled in sterile ampoules.

Hence, the F.1 formulation has the following composition:

| Sufentanil | 0.5 mg |
|---|---|
| Stearic acid | 0.37 mg |
| Benzyl alcohol | 15 mg |
| Miglyol 812 ® | 928 mg |

In a similar way, the following compositions were prepared:

| Formula F.2: Injectable solution - 0.4 mg/ml | |
|---|---|
| Sufentanil | 0.4 mg |
| Stearic acid | 0.294 mg |
| Miglyol 812 ® | 928 mg |
| Formula F.3: Injectable solution - 0.2 mg/ml | |
| Sufentanil | 0.2 mg |
| Stearic acid | 0.147 mg |
| Miglyol 812 ® | 928 mg |
| Formula F.4: Injectable solution - 0.5 mg/ml | |
| Sufentanil | 0.5 mg |
| Stearic acid | 0.37 mg |
| Benzyl alcohol | 15 mg |
| BHT | 0.25 mg |
| Miglyol 812 ® | 928 mg |

B. Pharmacokinetic Studies

Plasma Kinetics of Sufentanil in Beagle Dogs After Single Intramuscular Administration of a Sustained Release Formulation of Sufentanil

| Dosing | Three groups of seven male beagle dogs, weighing between 11 and 20 kg, were used in the experiment. A first group received a single intramuscular dose of 35 mg/kg body weight by injection of a 0.5 mg/ml sufentanil solution in Miglyol 812 ® (Formula F. 1 as described in the experimental part A) in the thigh muscle. A second group received under the same conditions a single intramuscular dose of 50 μg/kg body weight, and a third group received under the same |
|---|---|

-continued

| | |
|---|---|
| | conditions a single intramuscular dose of 70 μg/kg body weight. Owing to the precision of the dosing syringe (0.1 ml), administered doses differed less than 1% from the intended dose. |
| Sampling | Blood samples (5 ml on heparin 15–18 IU/ml blood) were taken from a jugular vein from the sufentanil treated dogs. Sampling was performed before (0 hours) and at 15, 30, 45, 60 and 90 minutes and at 2, 3, 4, 6, 8, 12, 24, 48 and 72 hours after dose administration. The blood samples were centrifuged at 3000 rpm for 10 minutes to allow plasma separation. |
| Analysis | Plasma samples were analyzed for sufentanil using a RIA method as described in Woestenborghs et al., Anesthesiology 1994, 80, 666–670. Mean plasma concentrations (in ng/ml) per dose level and per sampling time were calculated and are listed in Table 1. |

TABLE 1

| Post-dosing time | plasma concentration per dosage level (ng/ml) | | |
|---|---|---|---|
| (hours) | 35 μg/kg | 50 μg/kg | 70 μg/kg |
| 0 | ≦0.050 | ≦0.050 | ≦0.050 |
| 0.25 | 0.194 | 0.532 | 0.331 |
| 0.5 | 0.342 | 0.727 | 0.498 |
| 0.75 | 0.388 | 0.771 | 0.600 |
| 1 | 0.478 | 0.808 | 0.734 |
| 1.5 | 0.484 | 0.782 | 0.839 |
| 2 | 0.575 | 0.906 | 1.04 |
| 3 | 0.712 | 1.05 | 1.34 |
| 4 | 0.793 | 1.12 | 1.67 |
| 6 | 0.929 | 1.16 | 2.17 |
| 8 | 0.893 | 1.13 | 1.91 |
| 12 | 0.843 | 1.10 | 1.61 |
| 24 | 0.440 | 0.718 | 0.849 |
| 48 | 0.142 | 0.205 | 0.360 |
| 72 | ≦0.050 | ≦0.050 | 0.095 |

We claim:

1. A pharmaceutical composition suitable for intramuscular administration comprising a medium-chain triglyceride as a carrier and as an active ingredient an effective analgesic amount of a sufentanil, as an admixture with stearic acid, soluble in the medium-chain triglyceride.

2. A pharmaceutical composition according to claim 1 wherein the active ingredient comprises a salt of sufentanil with a $C_{8-22}$ carboxylic acid.

3. A pharmaceutical composition according to claim 1 wherein the active ingredient is the 1:1 salt of sufentanil with stearic acid.

4. A pharmaceutical composition according to claim 3 wherein the concentration of sufentanil form ranges from 0.1 mg/ml to 1 mg/ml.

5. A pharmaceutical composition according to claim 3 wherein the concentration of sufentanil ranges from 0.3 mg/ml to 0.8 mg/ml.

6. A pharmaceutical composition according to claim 3 wherein the concentration of sufentanil is 0.5 mg/ml.

7. A pharmaceutical composition according to claim 6 also comprising an antimicrobial or an antioxidizing agent, or a combination thereof.

8. A pharmaceutical composition according to claim 7 wherein the antimicrobial is benzyl alcohol.

9. A pharmaceutical composition according to claim 7 wherein the antioxidizing agent is BHT.

10. A pharmaceutical composition according to claim 1 wherein the medium-chain triglyceride is a triglyceride of caprylic and carpric acid.

11. A pharmaceutical composition comprising sufentanil stearic acid salt 1:1.

12. A method of treating pain comprising administering to a host in need thereof an effective amount of a composition of claim 1.

13. The method of claim 12 wherein the pain is post-operative pain.

14. A process for preparing a pharmaceutical composition as defined in claim 1, characterized in that a therapeutically effective amount of sufentanil, as an admixture with stearic acid, is mixed with the medium-chain triglyceride.

* * * * *